(12) United States Patent
Castro

(10) Patent No.: US 11,291,479 B2
(45) Date of Patent: Apr. 5, 2022

(54) SURGICAL FASTENER

(71) Applicant: Blue Sky Technologies, LLC, Louisville, KY (US)

(72) Inventor: Frank Castro, Louisville, KY (US)

(73) Assignee: BLUE SKY TECHNOLOGIES, LLC, Louisville, KY (US)

( * ) Notice: Subject to any disclaimer, the term of this patent is extended or adjusted under 35 U.S.C. 154(b) by 0 days.

(21) Appl. No.: 17/090,970

(22) Filed: Nov. 6, 2020

(65) Prior Publication Data

US 2021/0244449 A1 Aug. 12, 2021

Related U.S. Application Data

(60) Provisional application No. 62/975,248, filed on Feb. 12, 2020.

(51) Int. Cl.
| | |
|---|---|
| *A61B 17/70* | (2006.01) |
| *A61B 17/86* | (2006.01) |
| *A61B 17/16* | (2006.01) |
| *A61B 17/84* | (2006.01) |

(52) U.S. Cl.
CPC .......... *A61B 17/7055* (2013.01); *A61B 17/16* (2013.01); *A61B 17/7035* (2013.01); *A61B 17/84* (2013.01); *A61B 17/8605* (2013.01); *A61B 17/8625* (2013.01); *A61B 17/8635* (2013.01); *A61B 2017/8655* (2013.01)

(58) Field of Classification Search
CPC ..... A61B 17/7055; A61B 17/16; A61B 17/84; A61B 17/8605; A61B 17/8635

USPC .................... 606/246, 300; 623/17.11, 17.16
See application file for complete search history.

(56) References Cited

U.S. PATENT DOCUMENTS

| | | | |
|---|---|---|---|
| 6,309,421 B1 * | 10/2001 | Pisharodi | A61B 17/025 |
| | | | 623/17.16 |
| 7,871,441 B2 | 1/2011 | Eckman | |
| 8,083,799 B2 * | 12/2011 | Baynham | A61F 2/447 |
| | | | 623/17.16 |
| D742,517 S | 11/2015 | Schifano et al. | |
| 10,182,921 B2 * | 1/2019 | Georges | A61F 2/4455 |
| 10,603,185 B2 * | 3/2020 | Hovorka | A61F 2/4611 |
| 2004/0102847 A1 * | 5/2004 | Sato | A61F 2/447 |
| | | | 623/17.11 |
| 2004/0204714 A1 | 10/2004 | Liu | |
| 2008/0015695 A1 | 1/2008 | Eckman | |
| 2008/0051890 A1 * | 2/2008 | Waugh | A61F 2/442 |
| | | | 623/17.11 |
| 2008/0300634 A1 * | 12/2008 | Gray | A61B 17/7059 |
| | | | 606/280 |
| 2009/0248163 A1 * | 10/2009 | King | A61F 2/4611 |
| | | | 623/17.16 |
| 2015/0173917 A1 | 6/2015 | Radcliffe et al. | |
| 2019/0142601 A1 * | 5/2019 | Ashleigh | A61F 2/4611 |
| | | | 623/17.16 |

\* cited by examiner

*Primary Examiner* — Ellen C Hammond
*Assistant Examiner* — David C Comstock
(74) *Attorney, Agent, or Firm* — Business Patent Law, PLLC

(57) ABSTRACT

A surgical fastener for use in posterior surgeries that require fusion between the occiput and pelvis. Among other things, the surgical fastener includes a cutter for cutting bone or other tissue.

20 Claims, 2 Drawing Sheets

SURGICAL FASTENER

PRIORITY

Applicant claims the benefit of U.S. Provisional Application No. 62/975,248—Surgical Fastener—filed on Feb. 12, 2020.

BACKGROUND OF THE INVENTION

A. Field of the Invention

The present invention is surgical fastener provided with a wedge member, cutters, anterior tip and a head on the surgeon facing side of the surgical fastener. In select preferred embodiments, the head can be fixed or polyaxial. Other embodiments do not include the head. Except for the head, the surgical fastener is threadless.

B. Description of the Previous Art

Any discussion of references cited in this Description of the Previous Art merely summarizes the disclosures of the cited references and Applicant makes no admission that any cited reference or portion thereof is relevant prior art. Applicant reserves the right to challenge the accuracy, relevancy and veracity of the cited references.

References that may indicate a state-of-the-art include: 1) US Published Patent Application 20080015695-Eckman discloses a duel composition vertebral defect device; 2) U.S. Pat. No. 7,871,441-Eckman discloses a cervical fixation device; 3) US Published Patent Application 20040204714-Liu, et al.; 4) US Published Patent Application 20150173917-Radcliffe, et al. discloses an expandable spinal implant; and 5) US Design Patent D742517-Schifano, et al. discloses a spinal implant.

Among other things, none of the above listed references, alone or in combination, disclose a surgical fastener comprising: a) a wedge member comprising: i) four interconnected outward sides; ii) a tip connected with the anterior sides of the outward sides; a frontal edge of the tip adapted to engage a joint space or a portion of a surgically created cavity or the joint space; iii) a surgeon facing side connected to posterior ends of the interconnected outward sides, wherein a longitudinal axis extends from the tip through the surgeon facing side and the surgeon facing side comprises a greater cross-sectional area than a cross-sectional area of the frontal edge of the tip; iv) a first two opposed sides of the outward sides converging from the surgeon facing side toward the tip; v) a second two opposed sides converging from the surgeon facing side toward the tip; each of the second two opposed sides comprising at least two distinctive slopes between the surgeon facing side and the tip; and b) one or more cutters connected to the distinctive slopes connected with the surgeon facing side; the one or more cutters comprising a noncutting side perpendicular to the distinctive slopes and a slanted cutting side connected to the noncutting side and the distinctive slopes.

SUMMARY OF THE INVENTION

Successful fusion of a joint or broken bone is directly correlated to the construct rigidity surrounding the area of interest. Current spinal instrumentation relies on screws being anchored into bone and rods connecting to these anchors. Loosening of current constructs occurs primarily at the bone-anchor interface. Toggling of the screws can allow for enlargement of the insertion pathway. As the diameter of the insertion pathway increases, there is greater risk of the screw backing out and construct failure. The current invention can be utilized for arthrodesis procedures of the cervical, thoracic and lumbar spine, as well as the sacroiliac joint or other similar joints.

The biomechanical strength of traditional threaded fixation screws is dependent upon several design characteristics. Larger diameter screws are stronger and more difficult to extract due to increased surface area (friction). The thread pitch, or difference between the inner diameter and the outer diameter, also influences resistance to pull out or back out. The larger the pitch, the greater is the resistance to pull out. Biomechanical studies have demonstrated that the volume of bone between screw threads can influence the screw's resistance to pull out. Those skilled in the art recognize that the type and quality of bone are important variables influencing resistance to pull out. Patients with osteoporotic bone have significantly less dense bone than patients with normal bone densities. The contribution of the cancellous bone between the screw threads in patients with osteoporosis is less than patients of normal bone density. In some osteoporotic patients, the screw's fixation strength and resistance to pull out can be determined by the volume of cortical bone in one or two threads of a traditional fixation screw.

Long surgical constructs, such as those used for scoliosis or deformity correction surgery, are often anchored into the sacrum or ilium. These constructs are usually anchored with a large diameter threaded screw. The biophysical forces transmitted to these implanted screws can lead to loosening, construct failure, pain and additional revision surgery.

Many of traditional surgical screws include thread lengths of one to two millimeters that determine the screw's fixation strength. The current surgical fastener provides a potential fixation surface area of from about three to about ten times more than traditional fixation screws. In use, the potential surface area of the surgical fastener is generally juxtaposed the cortical bone—the patient's strongest bone. The current invention can be provided with surface treatments and apertures that can encourage bone ingrowth, long-tern construct stability and arthrodesis.

The anterior tapered tip can separate surfaces or a joint, such as the sacroiliac joint or posterior cervical joint or the frontal edge can cut cortical bone. When rotated, the surgical fastener can be adapted to cut cartilage, cortical bone or other tissues that can provide exposure of bone to another bony surface. Exposing two bony surfaces can increase the probability the bony surfaces uniting into a solid fusion. The cutter may facilitate reapproximation of two joint surfaces that have experienced a distractive deformity from trauma or tumor. Prior to cutting through the first articular surface, the cutter can guide the bone back towards its anatomic position. Once the cutter crosses both articular surfaces, forward pressure on the cutter compresses the two surfaces and the barbs prevent retropulsion. When a cutter is placed across a joint, it may also facilitate fusion by exposing a conduit for bone to form across the joint. When the cutter is positioned completely across a joint, it may compress the articular or bony surfaces. Such imposed motion limitation may result in joint ankylosis.

Among other things, the surgical fastener's head can: limit the depth the fastener can be inserted through the incision into the surgically created cavity or joint space; be connected with other surgical apparatus, such as, rods, plates or other fixation devices; and relative to a headless screw, apply increased torque to the cutter.

Intentional or unintentional rotation of threaded devices can lead to displacement of the device into or towards an undesirable location resulting in damage or dysfunction to either a nerve or blood vessel. Those skilled in the art recognize that expulsion of a surgical screw results in an unstable screw that can increase the risk of non-fusion or spinal deformity. Among other things, the surgical fastener can be provided with a head of sufficient area to prevent over-insertion into the surgically created cavity or joint space. Depending on medical and/or surgical parameters, the current invention can be adapted to either compress or distract a joint. By way of illustration, when distraction of the posterior cervical facet joint occurs, the adjacent neuroforamin is enlarged and indirect decompression of the exiting nerve root can occur. According to the current state-of-the art, threaded surgical screws cannot provide this benefit.

Subsequent to insertion into a surgically created cavity or joint space with adequate outward tissue remaining proximate the insertion point, rotating the surgical fastener from about from about 30 degrees to about 150 degrees can improve the surgical fastener's resistance to pull out forces.

Preferred embodiments of the surgical fastener can include an anterior tip, a wedge or wedge-like member with cutters and a head.

The anterior tip can separate surfaces or a joint, such as the sacroiliac joint or posterior cervical joint or the frontal edge can cut cortical bone. When rotated, the surgical fastener can be adapted to cut cartilage, cortical bone or other tissues that can provide exposure of bone to another bony surface. Exposing two bony surfaces can increase the probability of the bony surfaces uniting into a solid fusion. The wedge member may facilitate reapproximation of two joint surfaces that have experienced a distractive deformity from trauma or tumor. Prior to cutting through the first articular surface, the wedge member can guide the bone back towards its anatomic position. Once the wedge member crosses both articular surfaces, forward pressure on the wedge member compresses the two surfaces and the cutters prevent retropulsion. When the cutter is placed across a joint, it may also facilitate fusion by exposing a conduit for bone to form across the joint. When the cutter is positioned completely across a joint, it may compress the articular or bony surfaces. Such imposed motion limitation may result in joint ankylosis.

An aspect of the present invention is to provide a surgical fastener.

Still another aspect of the present invention is to provide a surgical fastener with a tip and a head opposite the tip.

It is yet another aspect of the present invention to provide a surgical fastener with either a fixed head or a polyaxial head.

Still another aspect of the present invention is to provide a surgical fastener with a receptacle adapted to receive an apparatus distinct from the surgical fastener.

It is still another aspect of the present invention to provide a surgical fastener with a wedge member.

Yet still another aspect of the present invention is to provide a surgical fastener with a wedge or wedge-like member having cutters positioned on outward surfaces of the wedge or wedge-like member.

Still another aspect of the present invention is to provide a surgical fastener where only the head is provided with threads.

A preferred embodiment of the current invention can be described as a surgical fastener comprising: a) a wedge member comprising: i) first, second, third and fourth interconnected outward sides; ii) a tip, connected with the first, second, third and fourth outward sides, positioned on the anterior side of and integral with the wedge member; the tip adapted to engage a joint space or a portion of a surgically created cavity or the joint space; iii) a surgeon facing side connected to posterior ends of the first, second, third and fourth outward sides, wherein the surgeon facing side comprises a greater cross-sectional area than a cross-sectional area of a frontal edge of the tip; iv) the first and third outward sides converging from the surgeon facing side toward the tip; v) the second outward side and the fourth outward side converging from the surgeon facing side toward the tip; each of the second and fourth outward sides comprising at least two distinctive slopes between the surgeon facing side and the tip; b) a receiver positioned in the surgeon facing side and adapted to receive an apparatus distinct from the surgical fastener; c) a longitudinal axis extending from the tip through the receiver; and d) one or more cutters connected to the distinctive slopes connected with the surgeon facing side; the one or more cutters comprising a noncutting side perpendicular to the distinctive slopes and a slanted cutting side connected to the noncutting side and the distinctive slopes.

Another preferred embodiment of the current invention can be described as a surgical fastener comprising: a) a wedge member comprising: i) four interconnected outward sides; ii) a tip adapted to engage a joint space or a portion of a surgically created cavity or the joint space; the tip positioned on the anterior side of the wedge member and interconnected with the outward sides; iii) a surgeon facing side connected to posterior ends of the interconnected outward sides, wherein the surgeon facing side comprises a greater cross-sectional area than a cross-sectional area of a frontal edge of the tip; iv) a first two opposed sides of the outward sides converging from the surgeon facing side toward the tip; v) a second two opposed sides converging from the surgeon facing side toward the tip; each of the second two opposed sides comprising at least two distinctive slopes between the surgeon facing side and the tip; b) a head connected with the surgeon facing side and adapted to receive an apparatus distinct from the surgical fastener; c) a longitudinal axis extending from the tip through the head; and d) one or more cutters connected to the distinctive slopes connected with the surgeon facing side; the one or more cutters comprising a noncutting side perpendicular to the distinctive slopes and a slanted cutting side connected to the noncutting side and the distinctive slopes.

Still another preferred embodiment of the current invention can be described as a surgical fastener comprising: a) a wedge member comprising: i) four interconnected outward sides; ii) a tip connected with the anterior sides of the outward sides; a frontal edge of the tip adapted to engage a joint space or a portion of a surgically created cavity or the joint space; iii) a surgeon facing side connected to posterior ends of the interconnected outward sides, wherein a longitudinal axis extends from the tip through the surgeon facing side and the surgeon facing side comprises a greater cross-sectional area than a cross-sectional area of the frontal edge of the tip; iv) a first two opposed sides of the outward sides converging from the surgeon facing side toward the tip; v) a second two opposed sides converging from the surgeon facing side toward the tip; each of the second two opposed sides comprising at least two distinctive slopes between the surgeon facing side and the tip; and b) one or more cutters connected to the distinctive slopes connected with the surgeon facing side; the one or more cutters comprising a noncutting side perpendicular to the distinctive slopes and a slanted cutting side connected to the noncutting side and the distinctive slopes.

It is the novel and unique interaction of these simple elements which creates the surgical fastener of the present invention. Pursuant to Title 35 of the United States Code, select preferred embodiments of the current invention follow. However, it is to be understood that the descriptions of the preferred embodiments do not limit the scope of the present invention.

DESCRIPTION OF THE PREFERRED EMBODIMENTS

Figure 1:
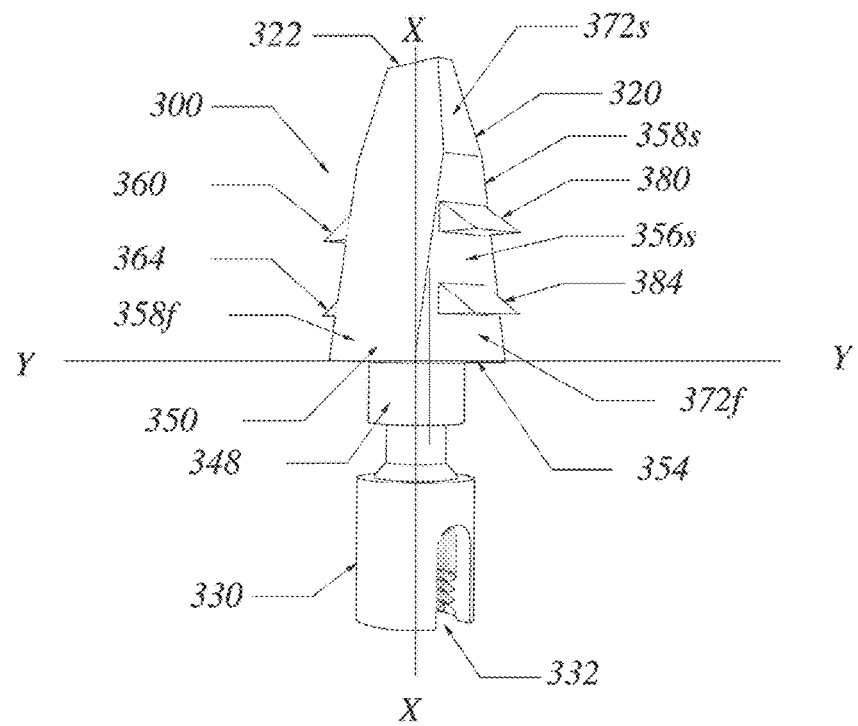
FIG. 1 is a perspective of a preferred embodiment of surgical fastener (300) including longitudinal axis X-X.

Although the disclosure hereof is detailed to enable those skilled in the art to practice the invention, the embodiments published herein merely exemplify the present invention.

As used herein, with respect to the surgical fastener (300): 1) "anterior" of the surgical fastener (300) means the side of the surgical fastener most distant from the surgeon and 2) "posterior or surgeon-facing side" of the surgical fastener (100) means the side of the surgical fastener nearest the surgeon.

In the most general sense, the present invention can result in joint arthrodesis where the surgical fastener is surgically inserted into or across a joint space. Depending on surgical parameters one or more surgical fasteners can be associated with the same surgically created cavity or joint space. The current surgical fastener can be useful for surgeries that can assist in stabilizing injured, deformed and or degenerative joints. Preferred embodiments of the current invention can be employed with ankle, cervical, hand, skull, sacroiliac or other orthopaedic procedures. It appears that the present system is particularly useful for posterior fusions from the occipital region to the pelvis, including the sacroiliac joints. However, the current invention can also be used to fuse the tibia to the talus, the talus to the calcaneus, and metacarpals to the phalanges.

Preferred embodiments of the current surgical fasteners can be manufactured of titanium alloys, stainless steel, non-resorbable polymers or any other composition acceptable in the art. Meeting a long felt but unfilled need in the orthopaedic surgical arts, the novel and unique structures of the present surgical fastener allow the surgical team to, among other things, simplify previous procedures.

The present invention has a wedge or wedge-like member with an anterior tip extending from an anterior end of the wedge member, one or more cutters attached to the wedge member and a head attached to the surgeon facing side of wedge member, all of which coincide with the longitudinal axis of the surgical fastener. Select preferred embodiments of the current surgical fastener do not include the head. The wedge member is capable of dissecting through adipose, muscle, bone, and/or joint capsule tissues. The wedge member is rotatable and can be a solid wedge member.

Cutters of the surgical fastener are capable of cutting cartilage and bone and can be associated with the creation of the surgical cavity. In select preferred embodiments, cutters are provided with a noncutting edge and a slanted cutter connected with the wedge member. The noncutting edge is generally perpendicular to the outward side of the wedge member to which the noncutting edge is attached. Further, the rotatable cutters can morselize bone in preparation for fusion. Select preferred embodiments of cutters of the current surgical fastener are generally slanted between an outward side of the wedge member and the noncutting edge. In other preferred embodiments of the wedge member can be provided with serrations for cutting.

A head is connected to the wedge member. The head can be provided with a receptacle and slots adapted to receive an apparatus distinct from the surgical fastener. Some preferred embodiments include an extender connecting the head to the wedge member. Depending on surgical requirements, the head can be either a fixed or polyaxial. And still other embodiments of the wedge member can be provided with a receiver adapted to receive an apparatus distinct from the surgical fastener.

The combination of the tip, wedge member, cutters and head of the surgical fastener meet long felt but unfilled needs in the orthopedic surgical arts of, among other things, allowing the surgeon to simplify the previous operating procedures utilized for posterior cervical, sacroiliac, and other joint fusions.

Figure 2:
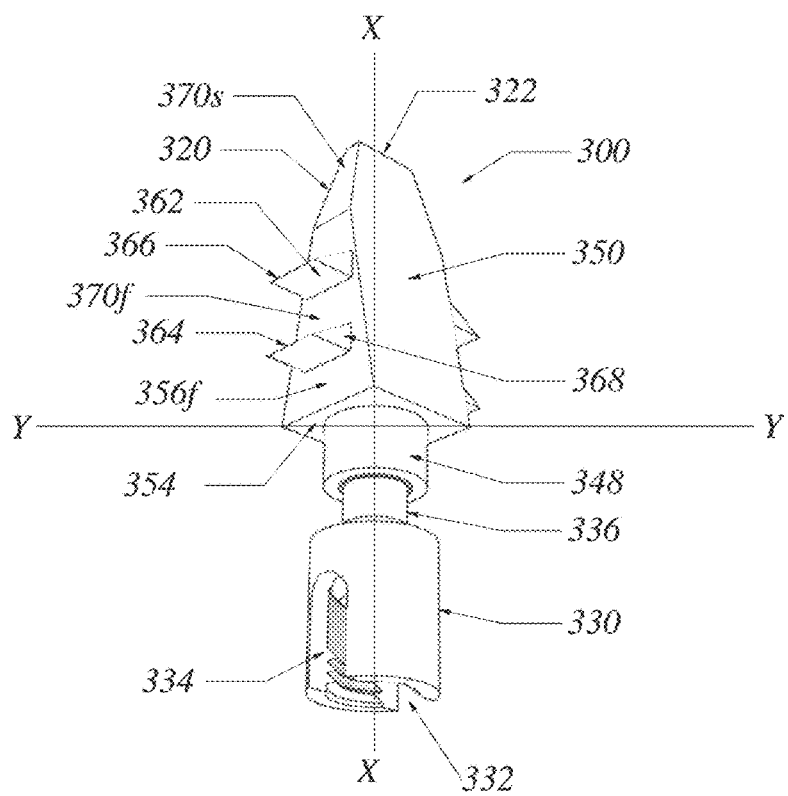
FIG. 2 is a second perspective of the FIG. 1 preferred embodiment of surgical fastener (300) where the surgical fastener (300) was rotated approximately 45 degrees.
Figure 3:
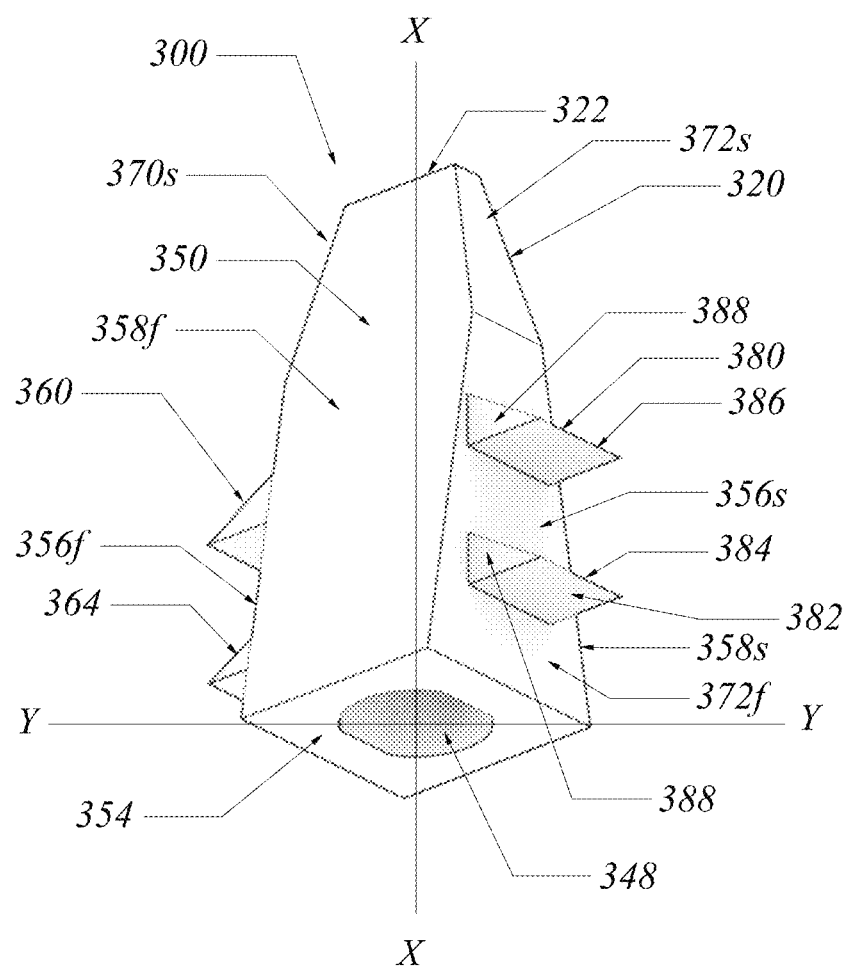
FIG. 3 is a perspective of a surgeon facing end (354) of wedge member (350) including a receiver (348).

FIGS. 1-3 are perspectives of surgical fastener (300). Among other things, surgical fastener (300) includes tip (320), head (330), wedge member (350), one or more first outward side cutters (360) and one or more second outward side cutters (380). The longitudinal axis X-X of wedge member (350) extends through tip (320) and surgeon facing side (354).

In select preferred embodiments of wedge member (350) can include first outward side (356f), second outward side (356s), third outward side (358f) and fourth outward side (358s). Tip (320) can be integral with wedge member (350) and positioned on anterior side of wedge member (350). Tip (320) is adapted to engage a joint space or a portion of a surgically created cavity or the joint space (not shown). Depending on surgical parameters, frontal edge (322) of tip (320) can be either dull or sharp.

Surgeon facing side (354) is connected to posterior ends of the first, second, third and fourth outward sides (356f, 356s, 358f, 358s). In preferred embodiments of wedge member (350), surgeon facing side (354) comprises a greater cross-sectional area than a cross-sectional area of a frontal edge (322) of tip (320).

Preferred embodiments of surgeon facing side (354) of wedge member (350) can include a receiver (348) therein or a head (330) connected thereto.

Head (330) can be connected to surgeon facing side (354), opposed from anterior or frontal edge (322) of wedge member (350). Head (330) is provided with receptacle (332) adapted to receive an apparatus (not shown) distinct from the surgical fastener (300). Receptacle (332) can be provided with one or more slots (334). Examples of apparatus received by receptacle (332) include insertion drivers that can advance the surgical fastener into or across a joint space, rods used to connect fasteners positioned at other spinal levels, and removal tools if surgical revision is required. Preferred embodiments of the current surgical fastener (300) can include fixed or polyaxial heads. When a polyaxial head (330) is utilized, an extender segment (336) extending from polyaxial head (330) and connected to surgeon facing side (354) of wedge member (350) can expand the multiplanar range of polyaxial head (330).

As shown in FIG. 3, second end (354) of wedge member (350) is provided with receiver (348) to receive an apparatus distinct from the surgical fastener (300). Use of receiver (348) can eliminate the use of head (330) in operation of the surgical fastener (300).

First outward side (358f) and third outward side (358s) converge toward each other from the surgeon facing side (354) toward the frontal edge (322) of tip (320). As shown in FIGS. 1-3, in select preferred embodiments, the convergence angles of each outward side (358f, 358s) are consistent. When engineering parameters require, in other embodiments of the surgical fastener (300), the convergence angles of each outward side (358f, 358s) can be variable.

Second outward side (356f) and the fourth outward side (356s) converge from the surgeon facing side (354) toward the frontal edge of (322) tip (320). In select preferred embodiments of wedge member (350), second outward side (356f) includes at least two distinctive slopes (370f, 370s) and fourth outward side (356s) is provided with at least two distinctive slopes (372f, 372s). The distinctive slopes (370f, 370s, 372f, 372s) extend between surgeon facing side (354) and tip (320). In select preferred embodiments of wedge member (350), distinctive slopes (370f, 370s, 372f, 372s) of second and fourth outward sides (356f, 358s) can include one or more trapezoidal planes.

One or more second outward side cutters (360) can be attached to distinctive slope (370f) of wedge member (350). Second outward side cutters (360) extend away from longitudinal axis X-X. Preferred embodiment of cutters (360) include noncutting sides (362) generally perpendicular to distinctive slope (370f) and slanted side (364) connected with noncutting side (362) and distinctive slope (370f). Second side cutters' (360) cutting edges include outer margins (366) distal from the longitudinal axis (X-X), lateral margins (368) connected with outer margins (366) and the slanted sides (364) connected with the noncutting sides (362). When medical conditions require, noncutting sides (362) can be attached to distinctive slope (370f) at angles other than perpendicular.

One or more fourth outward side cutters (380) can be attached to distinctive slope (372f) of wedge member (350). Fourth outward side cutters (380) extend away from longitudinal axis X-X. Preferred embodiment of cutters (380) include noncutting sides (382) generally perpendicular to distinctive slope (372f) and slanted side (384) connected with noncutting side (362) and distinctive slope (372f). Fourth side cutters' (380) cutting edges include outer margins (386) distal from the longitudinal axis (X-X), lateral margins (388) connected with outer margins (386) and the slanted sides (384) connected with the noncutting sides (382). When medical conditions require, noncutting sides (382) can be attached to distinctive slope (372f) at angles other than perpendicular. Within the scope of the current invention, first and second cutters (360, 380) can cut in either the clockwise or counterclockwise directions or both directions.

After insertion of the surgical fastener (300) through a surgical incision (not shown), engagement of the joint space or portion of the joint space or surgically created cavity (not shown) by the surgical fastener (300) and subsequent rotation of approximately 90 of degrees or more of wedge member (350) relative to an engagement point of the surgically created cavity or joint space by tip (320), surgical fastener (300) is positioned to resist pull out of surgical fastener (300) from the surgically created cavity or joint space.

Select preferred embodiments of the current invention have been disclosed and enabled as required by Title 35 of the United States Code.

What is claimed is:

1. A surgical fastener (300) comprising:
   a) a wedge member (350) comprising:
      i) first, second, third and fourth gapless interconnected outward sides (356f, 356s, 358f, 358s);
      ii) a tip (320), connected with the first, second, third and fourth outward sides (356f, 356s, 358f, 358s), positioned on the anterior side of and integral with the wedge member (350); the tip (320) adapted to engage a joint space or a portion of a surgically created cavity or the joint space;
      iii) a surgeon facing side (354) connected to posterior ends of the first, second, third and fourth outward sides (356f, 356s, 358f, 358s), wherein the surgeon facing side (354) comprises a greater cross-sectional area than a cross-sectional area of a frontal edge (322) of the tip (320);
      iv) the first and third outward sides (358f, 358s) converging from the surgeon facing side (354) toward the tip (320);
      v) the second outward side and the fourth outward side (356f, 356s) converging from the surgeon facing side (354) toward the tip (320); each of the second and fourth outward sides (356f, 356s) comprising at least two distinctive slopes (370f, 370s, 372f, 372s) between the surgeon facing side (354) and the tip (320);
   b) a receiver (348) positioned in the surgeon facing side (354) and adapted to receive an apparatus distinct from the surgical fastener (300);
   c) a longitudinal axis (X-X) extending from the tip (320) through the receiver (348); and
   d) one or more cutters (360, 380) connected to the distinctive slopes (370f, 370s, 372f, 372s) connected with the surgeon facing side (354); the one or more cutters (360, 380) comprising a noncutting side (362, 382) perpendicular to the distinctive slopes (370f, 370s, 372f, 372s) and a slanted cutting side (364, 384) connected to the noncutting side (362, 382) and the distinctive slopes (370f, 370s, 372f, 372s).

2. The surgical fastener of claim 1, wherein the one or more cutters are adapted to cut in a clockwise, counterclockwise or both directions.

3. The surgical fastener of claim 2, wherein, after insertion through a surgical incision, engagement of the surgically created cavity or joint space by the surgical fastener and subsequent rotation of approximately 90 of degrees or more of the wedge member relative to an engagement point of the wedge member's tip, the surgical fastener is positioned to resist pull out of the surgical fastener from the surgically created cavity or joint space.

4. The surgical fastener of claim 3, wherein at least some of the one or more cutters' cutting edges comprise outer margins distal from the longitudinal axis and lateral margins connected with the outer margins and the cutting and noncutting sides.

5. The surgical fastener of claim 1, wherein two of the distinctive slopes connected with the tip create second and fourth outward sides comprising a trapezoidal plane.

6. A surgical fastener comprising:
   a) a wedge member comprising:
      i) four gapless interconnected outward sides;
      ii) a tip adapted to engage a joint space or a portion of a surgically created cavity or the joint space; the tip positioned on the anterior side of the wedge member and interconnected with the outward sides;

iii) a surgeon facing side connected to posterior ends of the interconnected outward sides, wherein the surgeon facing side comprises a greater cross-sectional area than a cross-sectional area of a frontal edge of the tip;

iv) a first two opposed sides of the outward sides converging from the surgeon facing side toward the tip;

v) a second two opposed sides converging from the surgeon facing side toward the tip; each of the second two opposed sides comprising at least two distinctive slopes between the surgeon facing side and the tip;

b) a head connected with the surgeon facing side and adapted to receive an apparatus distinct from the surgical fastener;

c) a longitudinal axis extending from the tip through the head; and d) one or more cutters connected to the distinctive slopes connected with the surgeon facing side; the one or more cutters comprising a noncutting side perpendicular to the distinctive slopes and a slanted cutting side connected to the noncutting side and the distinctive slopes.

7. The surgical fastener of claim 6, wherein at least some of the one or more cutters are adapted to cut in a clockwise, counterclockwise or both directions.

8. The surgical fastener of claim 7, wherein, after insertion through a surgical incision, engagement of the surgically created cavity or joint space by the surgical fastener and subsequent rotation of approximately 90 of degrees or more of the wedge member relative to an engagement point of the wedge member's tip, the surgical fastener is positioned to resist pull out of the surgical fastener from the surgically created cavity or joint space.

9. The surgical fastener of claim 8 comprising an extender connecting the head with the surgeon facing side.

10. The surgical fastener of claim 9, wherein at least some of the one or more cutters' cutting edges comprise outer margins distal from the longitudinal axis and lateral margins connected with the outer margins and the cutting and noncutting sides.

11. The surgical fastener of claim 10, wherein the head is a polyaxial head.

12. The surgical fastener of claim 11, wherein two of the distinctive slopes connected with the tip comprise a trapezoidal plane.

13. A surgical fastener comprising:
a) a wedge member comprising:
i) four gapless interconnected outward sides;

ii) a tip connected with the anterior sides of the outward sides; a frontal edge of the tip adapted to engage a joint space or a portion of a surgically created cavity or the joint space;

iii) a surgeon facing side connected to posterior ends of the interconnected outward sides, wherein a longitudinal axis extends from the tip through the surgeon facing side and the surgeon facing side comprises a greater cross-sectional area than a cross-sectional area of the frontal edge of the tip;

iv) a first two opposed sides of the outward sides converging from the surgeon facing side toward the tip;

v) a second two opposed sides converging from the surgeon facing side toward the tip; each of the second two opposed sides comprising at least two distinctive slopes between the surgeon facing side and the tip; and b) one or more cutters connected to the distinctive slopes connected with the surgeon facing side; the one or more cutters comprising a noncutting side perpendicular to the distinctive slopes and a slanted cutting side connected to the noncutting side and the distinctive slopes.

14. The surgical fastener of claim 13, wherein at least some of the one or more cutters are adapted to cut in a clockwise, counterclockwise or both directions.

15. The surgical fastener of claim 14, wherein, after insertion through a surgical incision, engagement of the surgically created cavity or joint space by the surgical fastener and subsequent rotation of approximately 90 of degrees or more of the wedge member relative to an engagement point of the tip's frontal edge, the surgical fastener is positioned to resist pull out of the surgical fastener from the surgically created cavity or joint space.

16. The surgical fastener of claim 15, wherein at least some of the one or more cutters' cutting edges comprise outer margins distal from the longitudinal axis and lateral margins connected with the outer margins and the cutting and noncutting sides.

17. The surgical fastener of claim 16, wherein two of the distinctive slopes connected with the tip comprise a trapezoidal plane.

18. The surgical fastener of claim 16 comprising a head connected with the surgeon facing side and adapted to receive an apparatus distinct from the surgical fastener.

19. The surgical fastener of claim 18, wherein the head is a polyaxial head.

20. The surgical fastener of claim 16 comprising a receiver positioned in the surgeon facing side and adapted to receive an apparatus distinct from the surgical fastener.

* * * * *